(12) United States Patent
Belyakov et al.

(10) Patent No.: US 7,820,979 B2
(45) Date of Patent: Oct. 26, 2010

(54) PULSED ULTRAVIOLET ION SOURCE

(75) Inventors: Vladimir V. Belyakov, Podolsk (RU); Vladimir Kekukh, Chestnut Hill, MA (US); Anatoly Lazarevich, Lynn, MA (US); Stephen N. Bunker, Wakefield, MA (US)

(73) Assignee: Implant Sciences Corporation, Wilmington, MA (US)

( * ) Notice: Subject to any disclaimer, the term of this patent is extended or adjusted under 35 U.S.C. 154(b) by 343 days.

(21) Appl. No.: 12/151,273

(22) Filed: May 5, 2008

(65) Prior Publication Data

US 2009/0272896 A1 Nov. 5, 2009

(51) Int. Cl.
*H01J 49/10* (2006.01)
*H01J 49/12* (2006.01)

(52) U.S. Cl. .............. 250/423 R; 250/423 P; 250/424; 250/288; 250/281; 250/282; 438/961

(58) Field of Classification Search ............. 250/423 R, 250/424, 423 P, 288, 281, 282; 438/961
See application file for complete search history.

(56) References Cited

U.S. PATENT DOCUMENTS 5,300,773 A 4/1994 Davies
6,429,426 B1 8/2002 Döring
6,586,729 B2 7/2003 Döring
6,740,874 B2 5/2004 Döring
7,002,146 B2* 2/2006 Fischer et al. ............... 250/288
7,057,130 B2 6/2006 Gefter et al.
7,157,721 B1 1/2007 Blanchard
7,274,015 B2 9/2007 Miller et al.
7,304,298 B2 12/2007 Swenson et al.
7,326,926 B2 2/2008 Wang
7,576,322 B2* 8/2009 Karpetsky et al. ........... 250/288

OTHER PUBLICATIONS

Petr Lukes; Martin Clupek; Vaclav Babicky; Pavel Sunka: "Ultraviolet radiation from the pulsed corona discharge in water; UV radiation from the pulsed corona discharge in water", Plasma Sources Science and Technology, Institute of Physics Publishing, Bristol, GB, vol. 17, No. 2, May 1, 2008, p. 24012, XP020136953, ISSN: 0963-0252.

* cited by examiner

*Primary Examiner*—Nikita Wells
(74) *Attorney, Agent, or Firm*—Muirhead and Saturnelli, LLC (57) ABSTRACT

A system and method for providing a pulsed atmospheric source of ions for chemical analysis includes a chamber containing a pair of electrodes and a second chamber with the sample gas. A narrow pulse of high voltage is applied between the electrodes to form an arc which emits ultraviolet light directly into the sample gas chamber through an aperture connecting the chambers. The ultraviolet photons ionize the sample gas and the resultant sample gas ions are then swept into a chemical detector by an electric field.

26 Claims, 8 Drawing Sheets

PULSED ULTRAVIOLET ION SOURCE

BACKGROUND OF THE INVENTION

1. Field of the Invention

This application relates to the field of detection of chemical substances and, more particularly, to an ion source for providing ions to a chemical detector.

2. Description of Related Art

Chemical detection may be performed by a variety of detection instruments, such as a gas chromatograph, an ion mobility spectrometer, a mass spectrometer, and/or a differential mobility spectrometer. Many of these chemical detectors require that a chemical gas sample (the "sample gas") be ionized in an ion source prior to reaching the detection component. In many embodiments the ion source to ionize the sample gas is operated at atmospheric pressure (the "atmospheric ion source").

A variety of methods for ionizing the sample gas are known. A radioactive source, such as an alpha or beta source, may be employed. X-ray sources are known (see, for example, U.S. Pat. No. 6,429,426 entitled "Ionization chamber with electron source", U.S. Pat. No. 6,740,874 entitled "Ion mobility spectrometer with mechanically stabilized vacuum-tight x-ray window", and U.S. Pat. No. 6,586,729 entitled "Ion mobility spectrometer with non-radioactive ion source, all to Doring) in addition to photoelectric ion sources (see, for example, U.S. Pat. No. 7,304,298 to Swenson, et al., entitled "Photoemissive ion mobility spectrometry in ambient air" and U.S. Pat. No. 5,300,773 to Davies, entitled "Pulsed ionization ion mobility sensor"), ultraviolet lamp ion sources (see, for example, U.S. Pat. No. 7,002,146 to Fischer, et al., entitled "Ion sampling for APPI mass spectrometry"), and several kinds of corona sources. Corona sources are typically either continuous (DC) or radio frequency (AC) (see, for example, U.S. Pat. No. 7,057,130 to Gefter, et al., entitled "Ion generation method and apparatus", U.S. Pat. No. 7,274,015 to Miller et al., entitled "Capacitive discharge plasma ion source", and U.S. Pat. No. 7,157,721 to Blanchard, entitled "Coupled ionization apparatus and methods"). The sample gas is typically passed through the corona discharge region in order to utilize the accelerated electrons to produce the ionization. Corona discharge ion sources may exist as a single pair of electrodes or as a plurality of electrodes (see, for example, U.S. Pat. No. 7,326,926 to Wang, entitled "Corona discharge ionization sources for mass spectrometric and ion mobility spectrometric analysis of gas-phase chemical species") for greater reliability and lifetime. All of the above-noted references are incorporated herein by reference.

Ion sources that are radioactive require expensive and inconvenient disposal of the source material when no longer needed for service. X-ray sources have a limited lifetime of operation and are expensive to replace. Photoelectric ion sources do not readily produce both positive and negative ions. Ultraviolet lamps are relatively large due to the expensive UV-transmitting envelope. Ultraviolet lamp envelopes are electrically insulating and can become charged with static, affecting the nearby electric field and attracting a particulate coating that obscures the emission of light. Ultraviolet lamp envelopes are difficult to clean, because common solvents leave an ultraviolet-blocking surface coating when they dry. Corona sources may have lifetime limitations or have an output of ions in both quantity and species that is sensitive to the instantaneous path of the discharge.

Accordingly, it would be desirable to provide a system that addresses the above-noted issues and improves the production of ions for use with a chemical detector.

SUMMARY OF THE INVENTION

According to the system described herein, a method for providing a pulsed atmospheric source of ions for chemical analysis includes providing a first chamber for generating a pulsed source of ultraviolet radiation. First and second electrically-conducting electrodes may be provided in the first chamber. A gap may be provided to electrically separate the first and second electrically-conducting electrodes. A pulse of high voltage electricity may be triggered across the gap to form a pulsed arc within the first chamber. A second chamber may be provided containing a sample gas in optical communication with the pulsed arc through an open aperture to the first chamber. The sample gas in the second chamber may be ionized using the ultraviolet radiation produced by the pulsed arc in the first chamber. An electric field may be provided to sweep the resultant sample gas ions from the second chamber.

According further to the system described herein, an ion source includes a first chamber and first and second electrically-conducting electrodes disposed in the first chamber and electrically separated by a gap. A high voltage pulse forming circuit may provide a pulse of high voltage electricity across the gap to form a pulsed arc within the first chamber. A second chamber may contain a sample gas in optical communication with the pulsed arc through an open aperture to the first chamber, wherein the pulsed arc ionizes the sample gas in the second chamber with ultraviolet radiation produced by the pulsed arc in the first chamber. An electric field generator may provide an electric field to sweep resultant sample gas ions from the second chamber.

According further to the system described herein, a chemical detection system includes a chemical analysis device and an ion source coupled to the chemical analysis device. The ion source may include first and second electrically-conducting electrodes disposed in the first chamber and electrically separated by a gap. A high voltage pulse forming circuit may provide a pulse of high voltage electricity across the gap to form a pulsed arc within the first chamber. A second chamber may contain a sample gas in optical communication with the pulsed arc through an open aperture to the first chamber, wherein the pulsed arc ionizes the sample gas in the second chamber with ultraviolet radiation produced by the pulsed arc in the first chamber. An electric field generator may provide an electric field to sweep resultant sample gas ions from the second chamber to the chemical analysis device.

The electrically conducting electrodes may include at least one of a noble metal, a refractory metal, and metal alloys containing substantially these metals. Examples of these metals may include the group platinum, tungsten, iridium, lanthanum, rhenium, thorium, and/or zirconium. At least one of the electrodes may be at least in part coated with a metal that facilitates making an electrical connection. Examples of these coating metals may include copper, nickel, gold, platinum, chromium, silver, and alloys thereof. Further, there may be a plurality of pairs of electrodes disposed in the first chamber.

The gap between the electrodes may be less than 5 millimeters but greater than 1 millimeter. The triggered pulse of voltage may be greater than 1500V plus the length of the gap in millimeters times 1000 Volts per millimeter. The triggered pulse is formed by activating an electronic switch for a high voltage pulse forming circuit. The pulse of high voltage electricity is less than 1 millisecond in duration. The current of the pulse of high voltage electricity is limited by a resistor in series with the output of a high voltage transformer in the pulse forming circuit. The total energy of the pulse may be shared by a plurality of arc gaps.

As discussed herein, the sample gas may flow in a separate chamber from that of the first and second electrically-conducting electrodes. The optical communication between the ultraviolet-producing discharge and the sample gas may be through a plurality of apertures between the first and second chambers. Having the sample gas pass through a separate chamber from the chamber containing the discharge may be preferable to having the sample gas passing through the arc discharge.

It is known that an ultraviolet lamp may be used to ionize the sample gas in which the ultraviolet lamp may include an optically transparent sealed envelope in which a high voltage discharge is generated therein. A special gas may be sealed within the envelope that provides a spectrum enhanced in the ultraviolet portion of the spectrum. In an embodiment of the system described herein, there may be no sealed envelope, and the chamber containing the high voltage discharge may be optically coupled to the chamber containing the sample gas without a sealing window. This configuration permits a plurality of discharges in a small volume in order to enhance the output of the ultraviolet radiation and provide long term operational reliability.

BRIEF DESCRIPTION OF THE DRAWINGS

Embodiments of the system described herein are explained with reference to the several figures of the drawing, noted as follows.

DETAILED DESCRIPTION OF VARIOUS EMBODIMENTS

Referring now to the figures of the drawing, the figures comprise a part of this specification and illustrate exemplary embodiments of the described system. It is to be understood that in some instances various aspects of the system may be shown schematically or may be shown exaggerated or altered to facilitate an understanding of the system.

Figure 1:
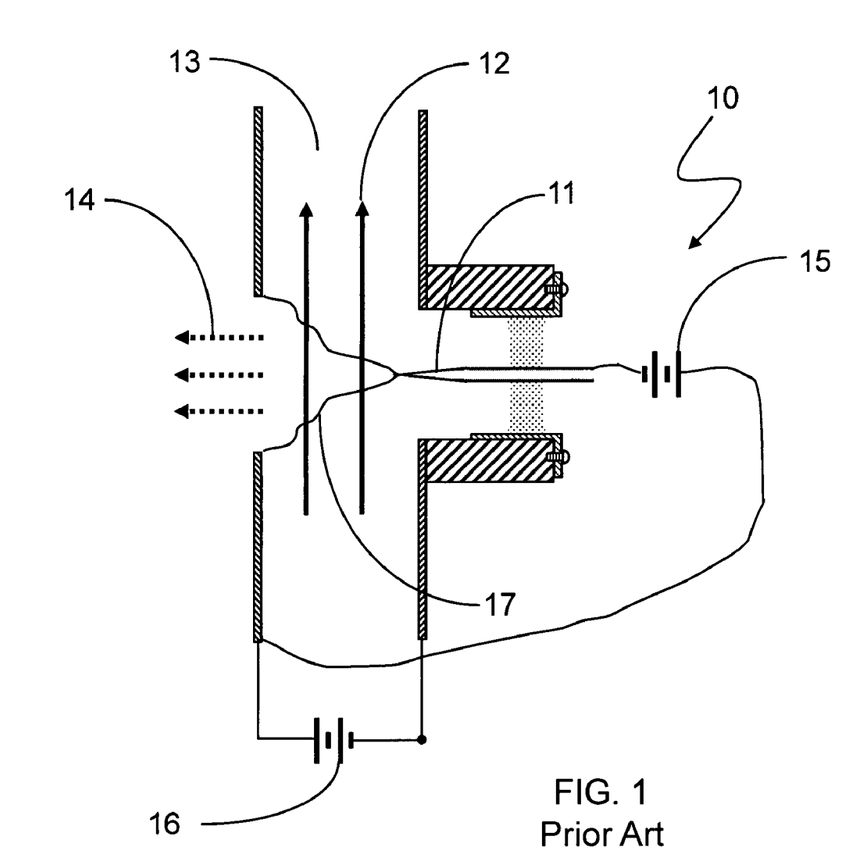
FIG. 1 is a diagram of a corona ion source known in the prior art.

In FIG. 1, an ion source 10 according to the prior art is shown that includes a chamber 13 with a flow of sample gas 12 that may contain a chemical for detection. An electrode 11 has a voltage applied from a high voltage source 15. A corona discharge 17 passes through the sample gas 12, ionizing the sample gas. A sweeping voltage 16 across the chamber 13 directs the ions with the polarity of interest 14 into the entrance to a chemical detector.

Figure 2:
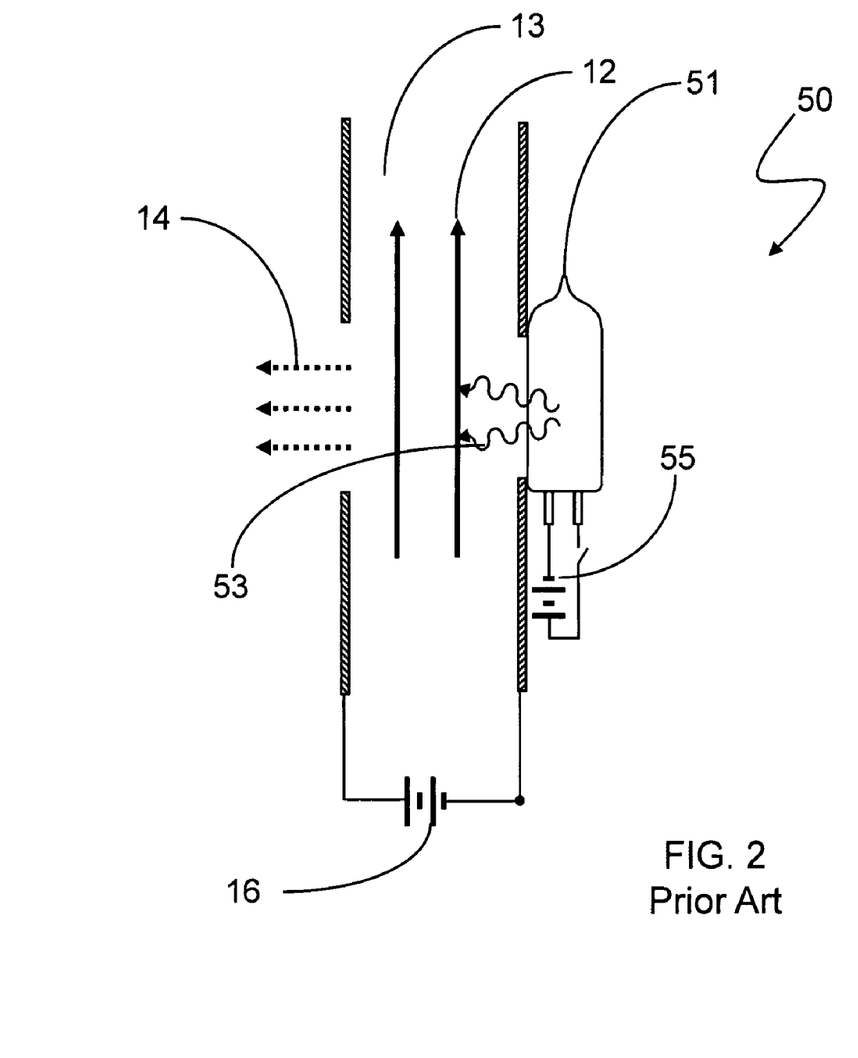
FIG. 2 is a diagram of an ultraviolet lamp ion source known in the prior art.

In FIG. 2, an ion source 50 according to the prior art is shown that includes a chamber 13 with a flow of sample gas 12 that may contain a chemical for detection. An ultraviolet lamp 51 has a voltage applied from a high voltage source 55 to provide an arc within the lamp to create ultraviolet emission 53 through the envelope of the lamp 51. The ultraviolet emission 53 passes through the sample gas 12, ionizing the sample gas. A sweeping voltage 16 across the chamber 13 directs the ions with the polarity of interest 14 into the entrance to a chemical detector.

Figure 3:
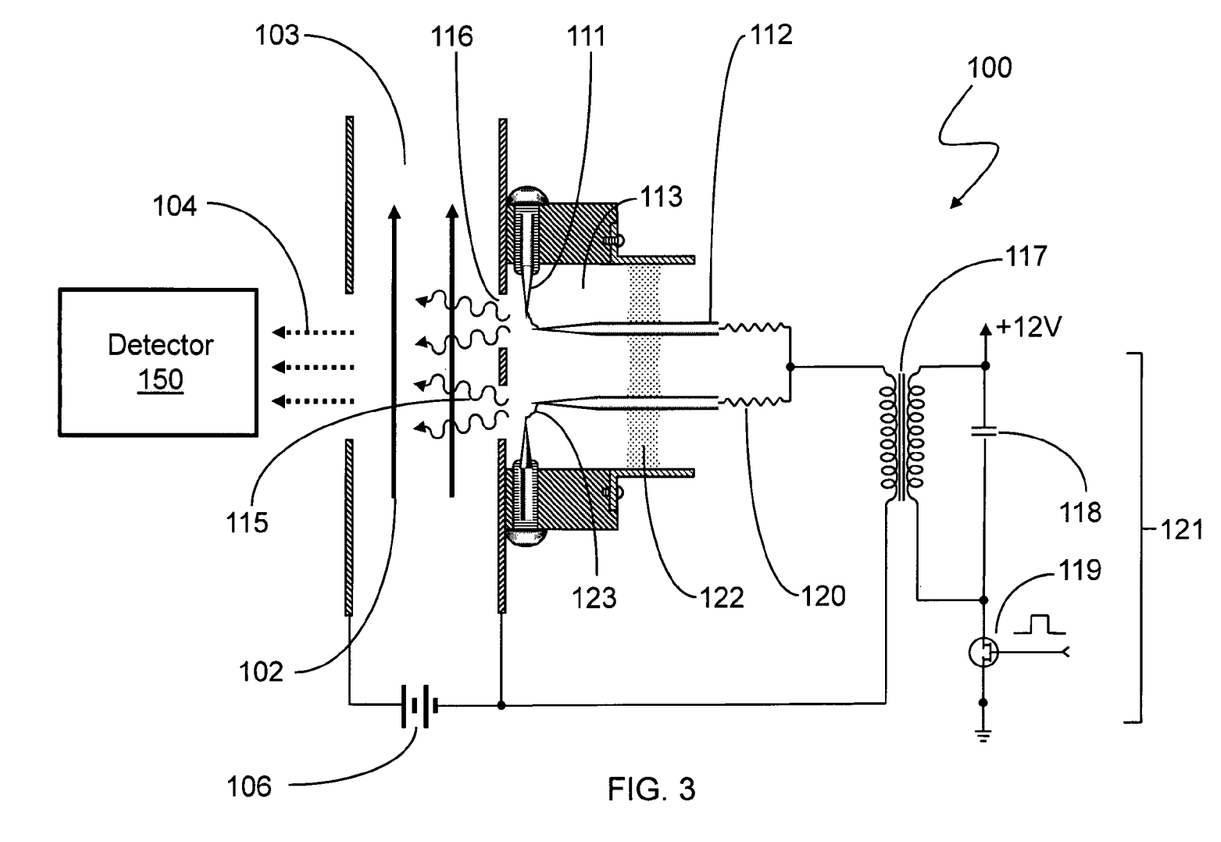
FIG. 3 is a schematic diagram illustrating fabrication of a pulsed ultraviolet light atmospheric ion source according to an embodiment of the system described herein.

FIG. 3 is a schematic diagram illustrating an ion source 100 that provides a pulsed atmospheric source of ions for chemical analysis according to an embodiment of the system described herein. The ion source 100 includes a chamber 103 with a flow of sample gas 102 that may contain a chemical for detection. The ion source 100 also includes a chamber 113 that contains a pair of electrodes 111 and 112 that are electrically separated by an air gap 123 and possibly additional insulation 122. A high voltage pulse is applied between the electrodes 111 and 112 from a high voltage pulsed power source 121. A corona discharge passes through the air gap 123, emitting ultraviolet radiation 115 through apertures 116 that provide optical communication between chambers 103 and 113. The ultraviolet radiation 115 ionizes the sample gas 102. A power supply 106 provides a sweeping voltage across the chamber 103 and directs the ions with the polarity of interest 104 into the entrance to a chemical detector 150. In an embodiment, the gap may have a length less than 5 millimeters but greater than 1 millimeter.

The high voltage pulse from the high voltage pulsed power source 121 may be provided by an electronic switch 119, which allows a current pulse into a high voltage step up transformer 117 and optional parallel capacitor 118. The resultant high voltage pulse may be current limited by a resistor 120 before being applied to the electrode 112. The high voltage pulse may be less than one millisecond in duration and may be greater than 1500V plus the length of the gap in millimeters times 1000 Volts per millimeter.

The electrodes 111, 112 may be made of a noble metal, a refractory metal, and metal alloys containing substantially these metals, and including, for example, platinum, tungsten, iridium, lanthanum, rhenium, thorium, and/or zirconium. Further, one or more of the electrodes may be at least in part coated with a coating metal that facilitates making an electrical connection. The coating metal may include copper, nickel, gold, platinum, chromium, silver, and/or alloys thereof. Although two sets of electrodes 111, 112 are illustrated, the system described herein may be used with one or multiple sets of electrodes disposed in the chamber 113 and in connection with other embodiments described herein.

Figure 4:
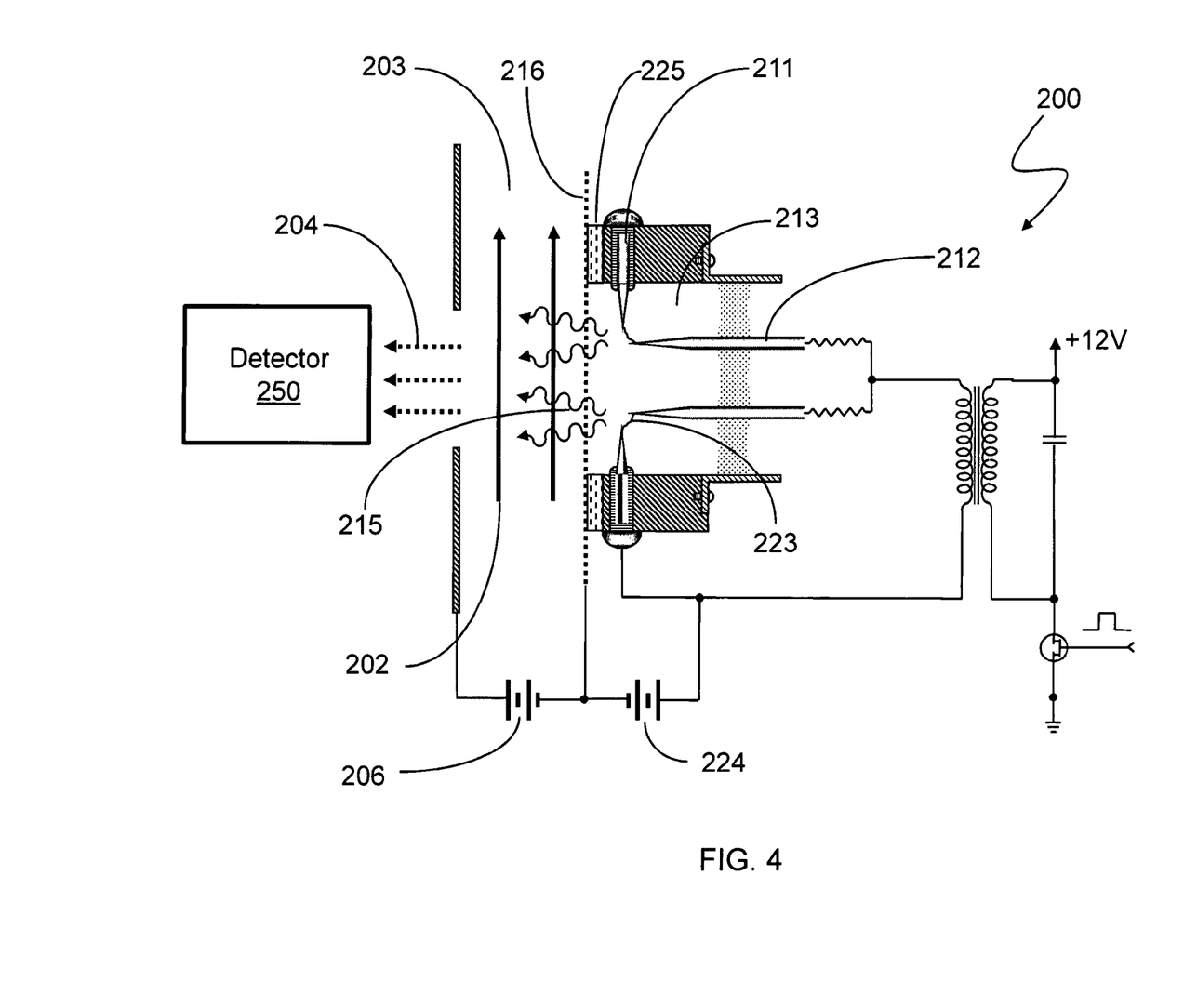
FIG. 4 is a schematic diagram illustrating a test configuration to demonstrate ultraviolet ionization produced by a pulsed ultraviolet light atmospheric ion source according to an embodiment of the system described herein.

FIG. 4 is a schematic diagram illustrating a test setup for an ion source 200 that provides a pulsed atmospheric source of ions for chemical analysis according to an embodiment of the system described herein. The test setup is designed to demonstrate that the ionization process is optical ionization by means of ultraviolet light, rather than by a corona discharge in sample gas as in FIG. 1. A chamber 203 with sample gas 202 is coupled by an open aperture 216 to another chamber 213, like the chamber 113 shown in the FIG. 3, and including therein electrodes 211, 212. With this configuration, it may be considered that sample gas 202 might be leaking into chamber 213 and ions made by the corona discharge in chamber 213 might be leaking back out into chamber 203. The test setup of FIG. 4 is designed to disprove this hypothesis.

In FIG. 4, the ion source 200 includes a metal mesh shielding grid 216 with a large plurality of small apertures, for example, that replaces the plate with apertures 116 shown in FIG. 3. A sweeping voltage from power supply 224 is applied to prevent ions of the polarity of interest that are produced by the corona discharge 223 from escaping chamber 213. An insulating ring 225 is positioned between the electrode 211 and the shielding grid 216. A power supply 206 provides a sweeping voltage across the chamber 203 that directs the ions with the polarity of interest 204 into the entrance of a chemical detector 250. If the only source of ions with the polarity of interest 204 was due to the corona discharge 223, then few ions would be observed in the chemical detector 250. The actual spectrum of ions is little changed as a result of this configuration, confirming that the origin of the ions 204 swept from chamber 203 is due to ionization by ultraviolet light 215.

Figure 5:
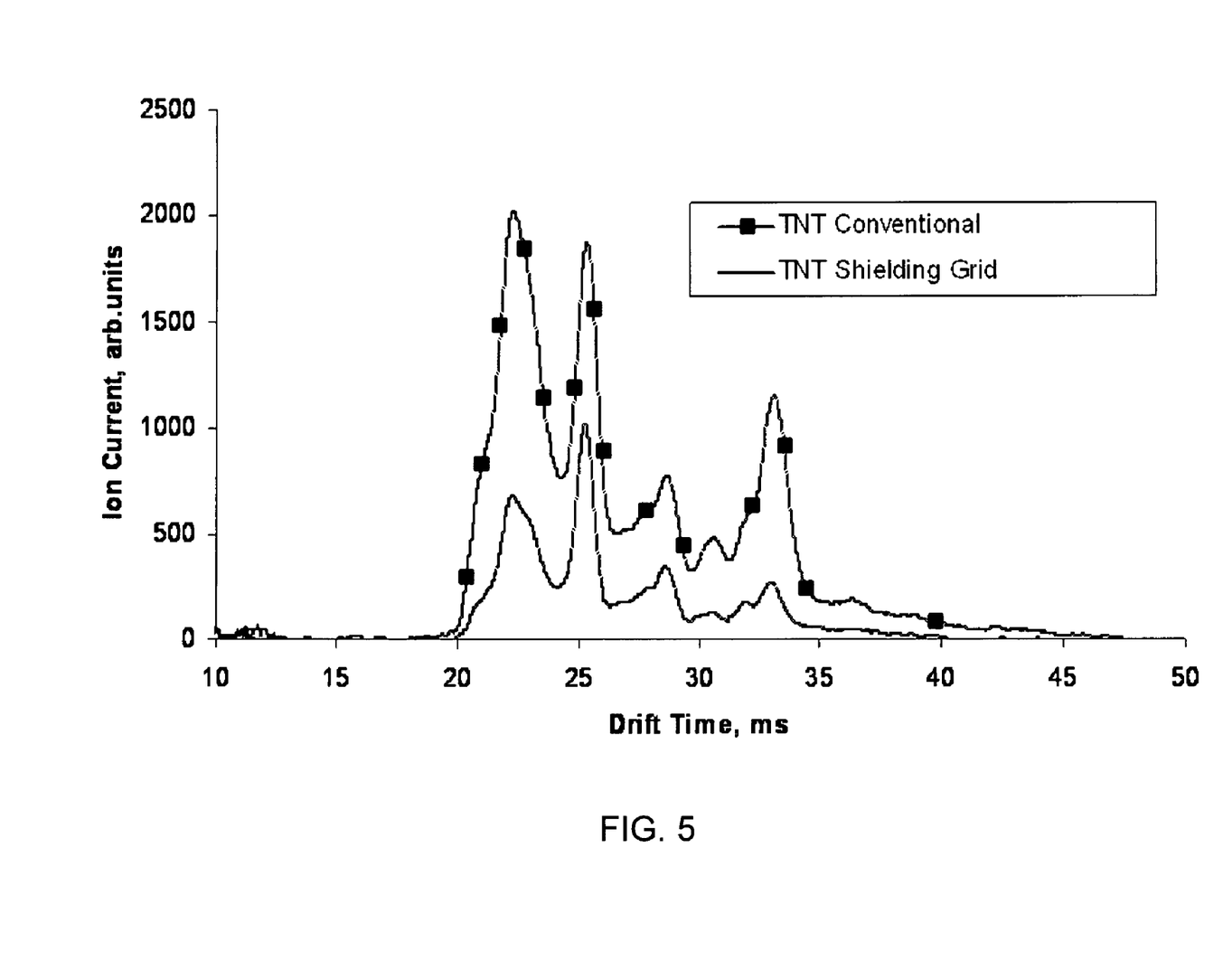
FIG. 5 is a schematic diagram illustrating two spectra of ions from a sample gas consisting of air plus TNT vapor according to the embodiments illustrated in FIGS. 3 and 4.

In FIG. 5, two spectra of ions are shown using an ion mobility spectrometer as the chemical detector. The ion source and the spectrometer are operated in a mode designed to detect negative ions. The vertical axis of the spectrum is proportional to the quantity of ions produced by an ion source that provides a pulsed atmospheric source of ions for chemical analysis according to an embodiment of the system described herein. Each peak in the spectrum represents at least one chemical species. The sample gas consisted of ambient air plus TNT vapor for both spectra. The higher amplitude spectrum labeled "TNT Conventional" is a spectrum using the ion source 100 geometry. The smaller amplitude spectrum labeled "TNT Shielding Grid" is for the ion source 200 geometry. Both spectra show the same peak structure even though the shielding grid 216 is preventing negative ions from passing from the chamber 213 into chamber 203 in the ion source 200. The difference in amplitude between the spectra is caused by the smaller transparency of the shielding grid 216 and the thickness of the insulating ring 225, which causes the corona discharge to be located further away from chamber 203, thus diminishing the intensity of the ionizing ultraviolet radiation 215 in chamber 203.

Figure 6:
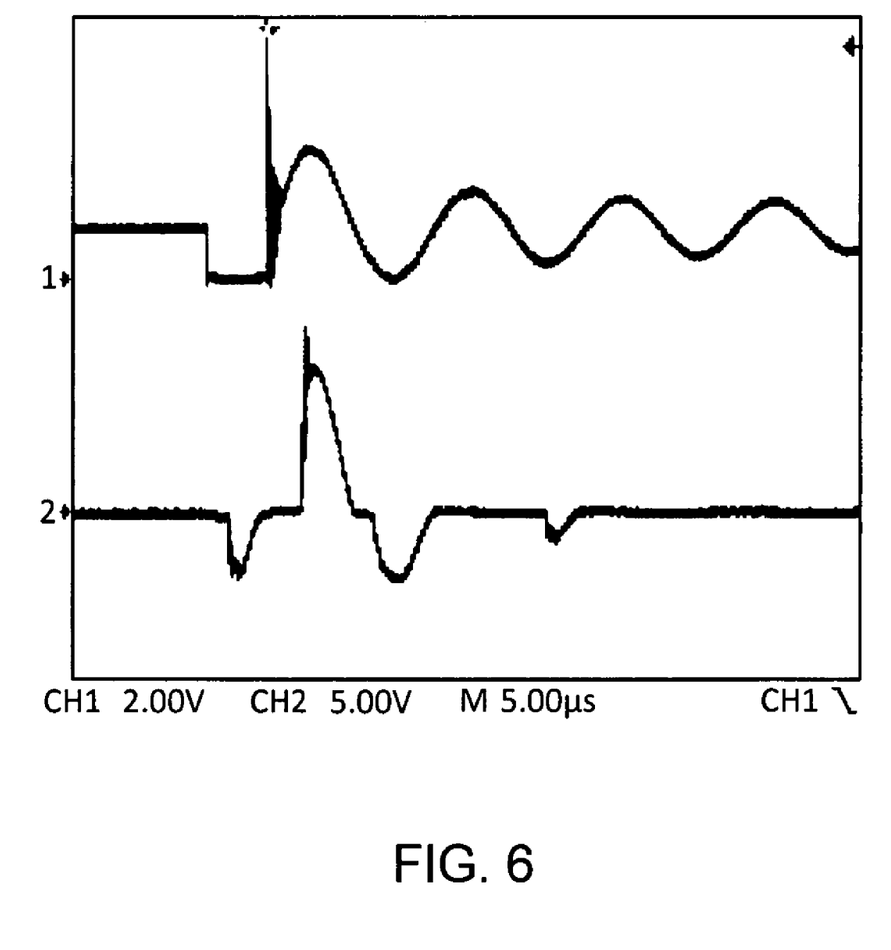
FIG. 6 is a schematic diagram illustrating the high voltage pulse waveform according to an embodiment of the system described herein.

In FIG. 6, the waveform of the pulsed high voltage is shown from an oscilloscope trace, illustrating the pulse of oscillating voltage with rapidly diminishing amplitude that results from the opening of an electronic switch into a high voltage pulse forming circuit.

Figure 7:
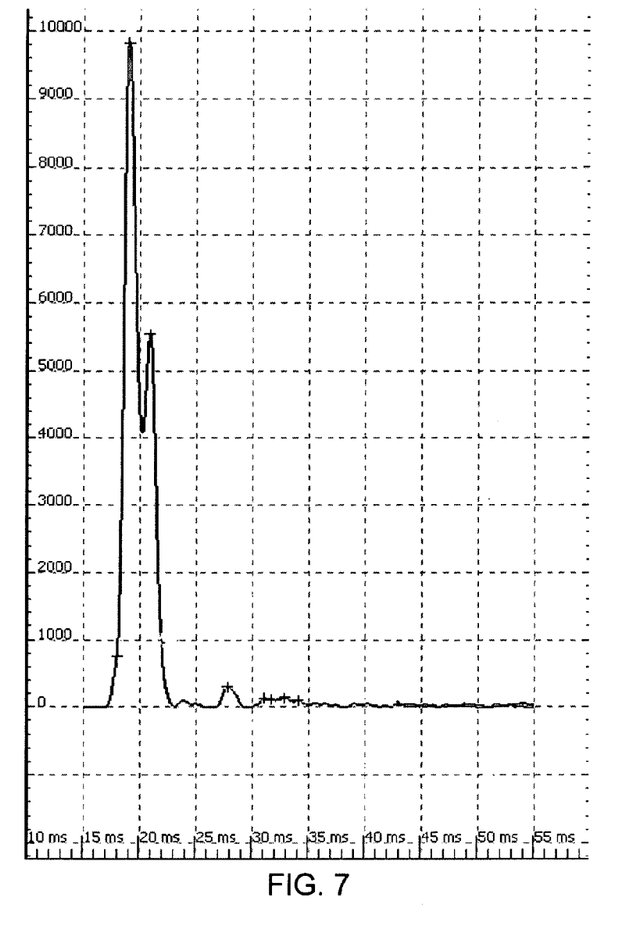
FIG. 7 is a schematic diagram illustrating a spectrum of ions from a sample gas consisting of air according to an embodiment of the system described herein.

In FIG. 7, a spectrum of ions is shown using an ion mobility spectrometer as the chemical detector. The vertical axis of the spectrum is proportional to the quantity of ions produced by the ion source 100 that provides a pulsed atmospheric source of ions for chemical analysis according to an embodiment of the system described herein. Each peak in the spectrum represents at least one chemical species. The sample gas included ambient air only.

Figure 8:
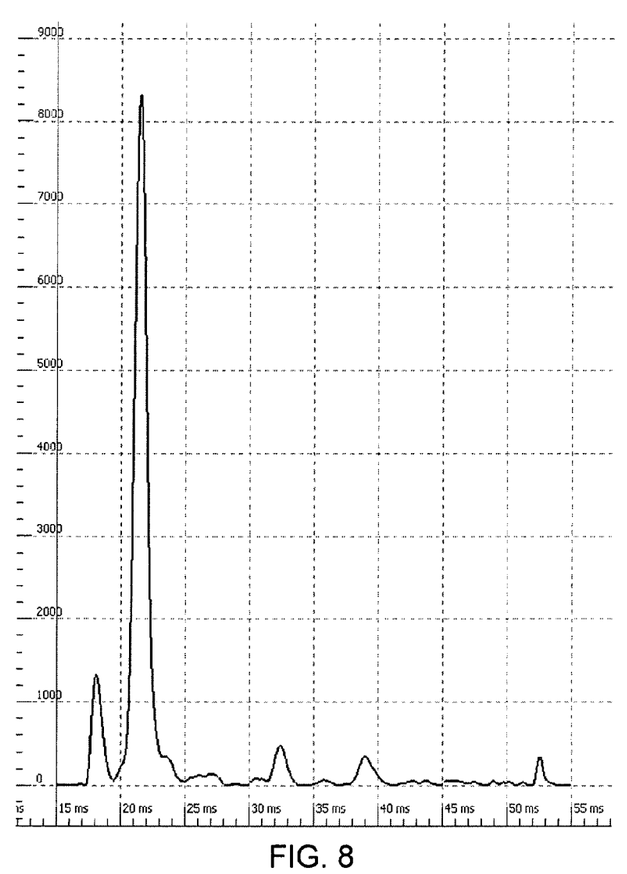
FIG. 8 is a schematic diagram illustrating a spectrum of ions from a sample gas including air and triacetone triperoxide according to an embodiment of the system described herein.

In FIG. 8, a spectrum of ions is shown using an ion mobility spectrometer as the chemical detector. The ion source 100 and the spectrometer are operated in a mode designed to detect positive ions. The vertical axis of the spectrum is proportional to the quantity of ions produced by the ion source 100 that provides a pulsed atmospheric source of ions for chemical analysis according to an embodiment of the system described herein. Each peak in the spectrum represents at least one chemical species. The sample gas included ambient air plus triacetone triperoxide (TATP) vapor. The tallest peak in the spectrum is related to TATP.

Embodiments of the system described herein may be incorporate other features, alone or in any combination, including without limitation features described in commonly-assigned U.S. patents: U.S. Pat. No. 7,098,672 to Belyakov, et al., entitled "Flash vapor sampling for a trace chemical detector", U.S. Pat. No. 7,244,288 to Belyakov, et al., entitled "Pulsed vapor desorber", U.S. Pat. No. 6,888,128 to Krasnobaev, et al., entitled "Virtual wall gas sampling for an ion mobility spectrometer", U.S. Pat. No. 6,870,155 to Krasnovaev, et al., entitled "Modified vortex for an ion mobility spectrometer", U.S. Pat. No. 6,861,646 to Motchkine, et al., entitled "Cyclone sampling nozzle for an ion mobility spectrometer", and U.S. Pat. No. 6,828,795 to Krasnobaev, et al., entitled "Explosive detection system", U.S. Published Patent App. No. 2006-0214580 A1 to Bunker, et al., entitled "Photoelectric ion source photocathode regeneration system", and U.S. Published Patent App. No. 2003-0155504 A1 to Motchkine, et al., entitled "Radiative sample warming for an ion mobility spectrometer", all of which are incorporated herein by reference.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for providing a pulsed atmospheric source of ions for chemical analysis, comprising:
providing a first chamber for generating a pulsed source of ultraviolet radiation;
providing first and second electrically-conducting electrodes in the first chamber;
providing a gap to electrically separate the first and second electrically-conducting electrodes;
triggering a pulse of high voltage electricity across the gap to form a pulsed arc within the first chamber;
providing a second chamber containing a sample gas in optical communication with the pulsed arc through an open aperture to the first chamber;
ionizing the sample gas in the second chamber using the ultraviolet radiation produced by the pulsed arc in the first chamber; and
providing an electric field to sweep the resultant sample gas ions from the second chamber.

2. The method according to claim 1, wherein the material of at least one of the first and second electrically-conducting electrodes is selected from a group consisting of: a noble metal, a refractory metal, and metal alloys containing substantially these metals.

3. The method according to claim 1, wherein the material for at least one of the first and second electrically-conducting electrodes is selected from a group consisting of: platinum, tungsten, iridium, lanthanum, rhenium, thorium, and zirconium.

4. The method according to claim 1, wherein at least one of the first and second electrically-conducting electrodes is coated at least in part with a coating metal that facilitates making an electrical connection.

5. The method according to claim 4, wherein the coating metal is selected from a group consisting of: copper, nickel, gold, platinum, chromium, silver, and alloys thereof.

6. The method according to claim 1, wherein the gap has a length less than 5 millimeters but greater than 1 millimeter.

7. The method according to claim 6, wherein the triggered pulse of voltage is greater than: 1500 Volts plus the length of the gap in millimeters times 1000 Volts per millimeter.

8. The method according to claim 1, wherein triggering is caused by operating an electronic switch for a high voltage pulse forming circuit.

9. The method according to claim 1, wherein the pulse of high voltage electricity is less than 1 millisecond in duration.

10. The method according to claim 1, wherein the current of the pulse of high voltage electricity is limited by a resistor in series with an output of a high voltage transformer.

11. The method according to claim 1, further comprising:
a plurality of pairs of first and second electrically-conducting electrodes in the first chamber.

12. The method according to claim 1, further comprising:
a plurality of open apertures between the first and second chambers that provides the optical communication.

13. An atmospheric ion source, comprising:
a first chamber;
first and second electrically-conducting electrodes disposed in the first chamber and electrically separated by a gap;
a high voltage pulse forming circuit that provides a pulse of high voltage electricity across the gap to form a pulsed arc within the first chamber;
a second chamber that contains a sample gas in optical communication with the pulsed arc through an open aperture to the first chamber, wherein the pulsed arc ionizes the sample gas in the second chamber with ultraviolet radiation produced by the pulsed arc in the first chamber; and
an electric field generator that provides an electric field to sweep resultant sample gas ions from the second chamber.

14. The ion source according to claim 13, wherein the pulse of high voltage electricity is greater than: 1500 Volts plus the length of the gap in millimeters times 1000 Volts per millimeter.

15. The ion source according to claim 13, wherein the pulse of high voltage electricity is less than 1 millisecond in duration.

16. The ion source according to claim 13, further comprising:
an electronic switch that triggers the high voltage pulse forming circuit.

17. The ion source according to claim 13, wherein the current of the pulse of high voltage electricity is limited by a resistor in series with an output of a high voltage transformer in the high voltage pulse forming circuit.

18. The ion source according to claim 13, further comprising:
a plate disposed between the first chamber and the second chamber, the plate including a plurality of open apertures that provides the optical communication between the first chamber and the second chamber.

19. The ion source according to claim 13, further comprising:
a plurality of pairs of first and second electrically-conducting electrodes in the first chamber.

20. A chemical detection system, comprising:
a chemical analysis device;
an atmospheric ion source coupled to the chemical analysis device, the ion source including:
first and second electrically-conducting electrodes disposed in the first chamber and electrically separated by a gap;
a high voltage pulse forming circuit that provides a pulse of high voltage electricity across the gap to form a pulsed arc within the first chamber;
a second chamber that contains a sample gas in optical communication with the pulsed arc through an open aperture to the first chamber, wherein the pulsed arc ionizes the sample gas in the second chamber with ultraviolet radiation produced by the pulsed arc in the first chamber; and
an electric field generator that provides an electric field to sweep resultant sample gas ions from the second chamber to the chemical analysis device.

21. The chemical detection system according to claim 20, wherein the pulse of high voltage electricity is greater than: 1500 Volts plus the length of the gap in millimeters times 1000 Volts per millimeter.

22. The chemical detection system according to claim 20, wherein the pulse of high voltage electricity is less than 1 millisecond in duration.

23. The chemical detection system according to claim 20, further comprising:
an electronic switch that triggers the high voltage pulse forming circuit.

24. The chemical detection system according to claim 20, wherein the current of the pulse of high voltage electricity is limited by a resistor in series with an output of a high voltage transformer in the high voltage pulse forming circuit.

25. The chemical detection system according to claim 20, further comprising:
a plate disposed between the first chamber and the second chamber, the plate including a plurality of open apertures that provides the optical communication between the first chamber and the second chamber.

26. The chemical detection system according to claim 20, further comprising:
a plurality of pairs of first and second electrically-conducting electrodes in the first chamber.

* * * * *